United States Patent
Kong et al.

(10) Patent No.: US 8,155,891 B2
(45) Date of Patent: Apr. 10, 2012

(54) INTEGRATED IN-LINE OIL MONITORING APPARATUS

(75) Inventors: Ho Sung Kong, Seoul (KR); Hung Gu Han, Seoul (KR); Liubou Vasilievna Markova, Gomel (BY); Vladimir Mikhailovich Makarenko, Gomel (BY); Mikhail Savich Semenyuk, Gomel (BY)

(73) Assignee: Korea Institute of Science and Technology, Seoul (KR)

( * ) Notice: Subject to any disclaimer, the term of this patent is extended or adjusted under 35 U.S.C. 154(b) by 449 days.

(21) Appl. No.: 12/389,942

(22) Filed: Feb. 20, 2009

(65) Prior Publication Data

US 2009/0216464 A1     Aug. 27, 2009

(30) Foreign Application Priority Data

Feb. 21, 2008  (KR) .................. 10-2008-0015944

(51) Int. Cl.
*G01N 33/30* (2006.01)
*G06F 17/40* (2006.01)

(52) U.S. Cl. ............ 702/25; 702/28; 702/32; 702/50; 356/70

(58) Field of Classification Search .......... 702/25, 702/28, 30, 31, 32, 50, 134
See application file for complete search history.

(56) References Cited

U.S. PATENT DOCUMENTS

| | | | | |
|---|---|---|---|---|
| 6,151,108 | A * | 11/2000 | Kwon et al. | 356/70 |
| 6,223,589 | B1 * | 5/2001 | Dickert et al. | 73/61.45 |
| 6,286,363 | B1 | 9/2001 | Discenzo | |
| 6,561,010 | B2 | 5/2003 | Wilson | |
| 2005/0072217 | A1 | 4/2005 | Discenzo | |
| 2007/0187617 | A1 * | 8/2007 | Kong et al. | 250/461.1 |
| 2008/0024761 | A1 * | 1/2008 | Kong et al. | 356/70 |

FOREIGN PATENT DOCUMENTS

| | | |
|---|---|---|
| JP | 07-318482 | 12/1995 |
| KR | 10-0789724 | 8/2007 |
| KR | 10-0795373 B1 | 1/2008 |

OTHER PUBLICATIONS

Hosung Kong, et al., "An experimental study on the measurement of water content in an lubricating oil by implementing a dew-point condensation sensor," International Symposium on Vehicle Tribology, Daegu, Korea, Nov. 11-12, 2004.

* cited by examiner

*Primary Examiner* — Hal Wachsman
(74) *Attorney, Agent, or Firm* — NSIP Law

(57) ABSTRACT

Various embodiments of an oil monitoring apparatus are provided. In one embodiment, an oil monitoring apparatus includes a probe and an analyzing module in-line connected to the probe. The probe includes: a first sensor for measuring respective optical intensities of a light passing through the oil at respective red, green and blue wavelength ranges; a second sensor for measuring a water content; and a third sensor for measuring a temperature of the oil. The analyzing module calculates and monitors chemical deterioration of the oil, total contamination of the oil, a relative saturation of the oil by water and temperature of the oil based on the output signals of the first and third sensors. The oil monitoring apparatus monitors various parameters relating to the deterioration of the oil and to the physical properties of the oil.

22 Claims, 9 Drawing Sheets

INTEGRATED IN-LINE OIL MONITORING APPARATUS

The present application claims priority from Korean Patent Application No. 10-2008-0015944, filed Feb. 21, 2008, the entirety of which is hereby incorporated by reference.

BACKGROUND

Historically, oil analysis was an off-site strategy handled by commercial laboratories. However, oil analysis has recently been viewed as a tool for managing a core asset, and on-site oil analysis has experienced rapid growth in many industrial fields.

As technology has advanced, more low-priced sensors have been introduced in the market. The purpose of these sensors is to measure the conditions of a machine in real-time and to provide analysts with highly reliable detailed information on the service life of the machine. However, analysis techniques using such sensors usually only measure a single parameter. Also, such techniques require use of the same lubricant or assume no machinery malfunctions during the measurement of a single parameter. As a result, such single-parameter sensors merely provide a narrow view on quality and/or health of a lubricant. However, it is virtually impossible to assess accurate lubricant health and to predict service intervals therefore by sensing a single parameter of the lubricant. Accordingly, to unambiguously identify any damage to the machine or the deteriorated state of the oil, it is important to measure a set of as many different parameters as possible. An integrated monitoring system may provide estimation of oil conditions/contamination and wear particle contents of oil in real time. Such a system may have directly built-in oil circulation lines of a machine or may be used like portable detectors in fields and laboratories. To monitor critical and expensive equipment, diagnostics based on standard oil parameters is needed in a number of cases.

In this regard, U.S. Pat. No. 6,561,010 describes a machine fluid analysis system that measures oil parameters similar to those obtained by standard laboratory machine fluid analysis. The system includes a viscometer (for viscosity), an energy dispersive X-ray fluorescence (EDXRF) spectrometer utilizing isotopic or X-ray tube X-ray sources (for elemental analysis), non-dispersive IR/visible light meter (for oxidation, nitration and turbidity). Analyzed oil is fed from monitored equipment through oil line/pipe to the system. The oil passes through a cooler before feeding into the EDXRF. Measurement of viscosity provides an indication of possible dilution of the oil by fuel or water. Viscosity can also indicate oil degradation from heat or oxidation. Chemical degradation of the oil (oxidation, nitration, etc.) is commonly determined by IR spectrometric analysis, as well as TAN and TBN analyses for the oil. Water in the oil is also detected by IR analysis. Slow coolant leaks into the lubricating oil system may be detected by EDXRF analysis of Boron, Chromium or other elements such as Iodine or Strontium added to the coolant water as salts. A controller that includes a microprocessor, memory, digital input/output, analog input, and mass storage, is used for controlling the system and collecting measured data. A modem is used to make on-board in situ information available to a remote observer of machine health. The system can provide a reliable conclusion to health condition of machine. However, due to its complexity and high price, the system is rather restrictively employed and may only be justified for monitoring critical industry equipment.

Further, as a state-of-the-art technology, modular systems with low cost sensors, which are sensitive elements integrated on a single substrate, have been developed. For example, U.S. Pat. No. 6,286,363 and U.S. Patent Application Publication No. 2005-0072217 describe a modular lubrication sensor, which is made using integrated circuit-like microfabrication techniques (silicon-based fabrication and deposition techniques). The lubrication sensor includes a semiconductor silicon base, on which a pH sensor, a chemical sensor, an electrical conductivity sensor and a temperature sensor are deposited. The pH sensor includes a reference electrode made of AgCl and a pH electrode made of palladium-palladium oxide (Pd—PdO). The chemical sensor is of a 3-electrode configuration, which includes a working electrode made of Ag, a reference electrode made of AgCl, and a counter electrode made of Ag. When either an AC or DC voltammetric signal is applied to the working electrode, a response current is generated between the working electrode and the counter electrode. The response current signal parameters vary depending upon the electrochemical processes occurring at the surface of the working electrode. The electrochemical processes are a function of the constituent concentrations, and the response current is therefore responsive to these concentrations. The electrochemical sensor determines the presence of water or oxidation in the lubricant. The electrical conductivity sensor consists of two electrodes and made of gold. The conductivity is used to determine metal wear and/or water present in the lubricant. The temperature sensor is platinum zone patterned on the base in accordance with a predetermined length, width and surface area.

Other modular sensors, which use a similar integrated circuit technology, are available in the market, but their reliability is rather low.

Consequently, there remains a strong need to develop reliable sensors, which provide adequate information and diagnostic capability, in order to develop modular systems with multi-function outputs.

SUMMARY

Various embodiments of an oil monitoring apparatus are provided. In one embodiment, by way of non-limiting example, an oil monitoring apparatus includes: a housing, a first sensor, a second sensor, a third sensor and a control unit including a processor. The housing may be mounted to a member containing oil therein so as to be in contact with the oil. The first sensor may be mounted to the housing and may include an optical passing element, a light-emitting means and a color-sensing means. The optical passing element may have an interface being in contact with the oil. The light-emitting means may emit a light to the optical passing element. The color-sensing means may measure respective optical intensities at respective red, green and blue wavelength ranges of a light passing through the oil via the optical passing element and the interface and output respective signals. The second sensor may be mounted to the housing for measuring a water content of the oil and outputting a signal. The third sensor may be mounted to the housing for measuring a temperature of the oil and outputting a signal. The processor may be configured to calculate a ratio value and a variation value from the output signals of the color-sensing means. The ratio value may be defined by a ratio of an optical intensity at the red wavelength range to an optical intensity at the green wavelength range. The variation value may be defined by respective variations in optical intensity at the respective red, green and blue wavelength ranges between an initial condition and a current condition of the oil. The processor may be configured to further calculate a relative saturation of the oil by water from the output signals of the second sensor and a temperature value of the oil from the output signals of the third sensor. The processor may be configured to monitor the ratio value, the variation value, the relative saturation and the temperature value.

In another embodiment, an oil monitoring apparatus including a probe and an analyzing module is provided. The probe may include: a housing mounted to a member containing oil therein so as to be in contact with the oil; a first sensor mounted to the housing for measuring optical intensities of a light passing through the oil and outputting signals; a second sensor mounted to the housing for measuring a water content of the oil and outputting a signal; and a third sensor mounted to the housing for measuring a temperature of the oil and outputting a signal. The first sensor may includes: an optical passing element with an interface being in contact with the oil; a light-emitting means for emitting a light to the optical passing element; and a color-sensing means for measuring respective optical intensities at respective red, green and blue wavelength ranges of a light passing through the oil via the optical passing element and the interface and outputting respective signals. The analyzing module may be configured to analyze conditions of the oil. The analyzing module may be in-line connected to the sensors. The analyzing module may include a control unit including a processor for calculating the output signals of the first to third sensors. The processor may be configured to calculate a first parameter and a second parameter from the output signals of the first sensor, a third parameter from the output signals of the second sensor and a fourth parameter from the output signals of the fourth sensor. The first parameter may be defined by a ratio value of an output at the red wavelength range to an output at the green wavelength range. The second parameter may be defined by a variation value in optical intensity at the respective red, green and blue wavelength ranges between an initial condition and a current condition of the oil. The third parameter may be defined by a relative saturation of the oil by water. The fourth parameter may be defined by a temperature of the oil. The processor may be configured to compare the first to fourth parameters with respective threshold values thereof.

The Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

Arrangements and embodiments may be described in detail with reference to the following drawings in which like reference numerals refer to like elements and wherein.

DETAILED DESCRIPTION

A detailed description may be provided with reference to the accompanying drawings. One of ordinary skill in the art may realize that the following description is illustrative only and is not in any way limiting. Other illustrative embodiments may readily suggest themselves to such skilled persons having the benefit of this disclosure.

The oil monitoring apparatus of the present disclosure may measure and monitor deterioration of oil and physical properties of the oil that can affect operation of equipment using the oil in real-time. To measure such deterioration and physical properties of the oil, the oil monitoring apparatus of the present disclosure may utilize four parameters that define the deterioration and the physical properties of the oil. The first parameter may be associated with chemical deterioration such as oxidative and thermal deterioration. The second parameter may be associated with total contamination of the oil, which results from physical contaminants (e.g., worn out particles, bubbles, etc.) and chemical contaminants (e.g., by-products caused by oxidative and thermal deterioration). The third parameter may be associated with relative saturation (RS) of oil by water, which can corrode the equipment. The fourth parameter may be associated with oil temperature, which can degrade the quality of the lubrication oil or otherwise cause damage by misalignment of the equipment. In embodiments of the oil monitoring apparatus, data for determining those parameters may be obtained in real time and on-site through a detecting device mounted on a component of the equipment containing the oil therein. An analyzing device, which may be connected to the detecting device in-line, may produce and monitor each of the parameters from the obtained data.

Figure 1:
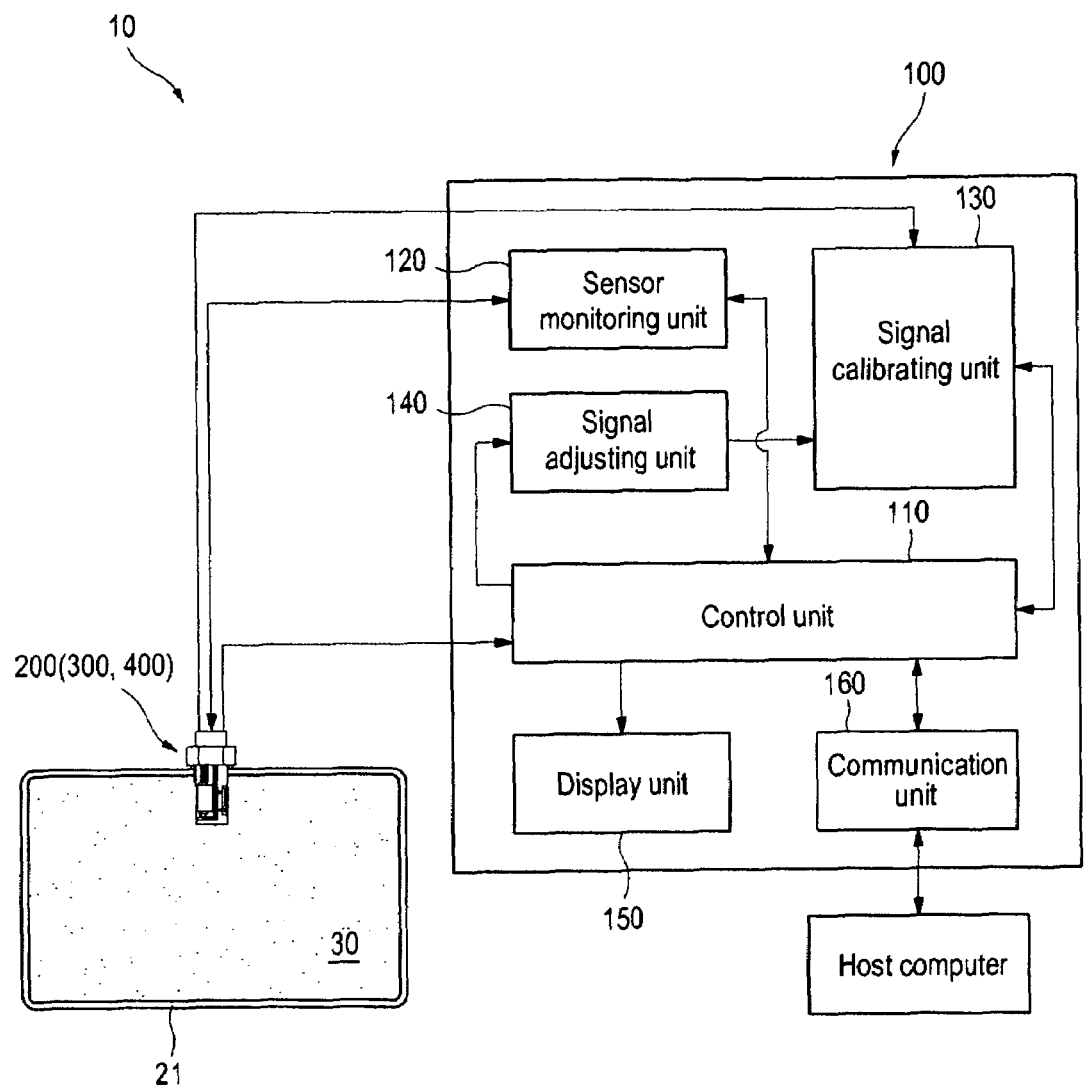
FIG. 1 is a schematic block diagram showing an illustrative embodiment of an oil monitoring apparatus according to the present disclosure.

FIG. 1 is a schematic block diagram showing an illustrative embodiment of the oil monitoring apparatus according to the present disclosure. Referring to FIG. 1, oil monitoring apparatus 10 may include: a module 100 for calculating the four parameters and analyzing states of the oil (hereinafter referred to as analyzing module 100); and a probe 200 for detecting deterioration and physical properties of the oil. It is understood that probe 300 or probe 400 may also be interchangeably used in place of probe 200 (such interchangeability hereinafter indicated as "probe 200, 300 or 400"). Oil monitoring apparatus 10 may be attached to equipment using and monitoring the oil. Such equipment may include, but is not limited to, a hydraulic system, a transformer, a turbine, a compressor, a gasoline engine, a diesel engine, etc. The oil may include, but is not limited to, hydraulic oil, transformer oil, turbine oil, compressor oil, engine oil, various lubricating oil, etc.

Probe 200, 300, or 400 may be mounted to a wall of an oil tank 21, which may be attached to equipment using the oil and contain oil 30 therein. Probe 200, 300, or 400 may be provided with first, second and third sensors for detecting the current conditions of the oil and outputting signals. The signals outputted from the first, second and third sensors may be transferred to analyzing module 100 and be processed therein. Analyzing module 100 may monitor the deterioration of the oil as well as variation in physical properties of the oil, which can affect the operations of the equipment, in real-time based on the output signals of the sensors.

It is illustrated in FIG. 1 that probe 200, 300, or 400 is mounted to oil tank 21. However, probes 200, 300, or 400 may be attached to an oil circulation line, an oil circulation pipe and the like (equipment that utilizes the oil to be analyzed).

Figure 2:
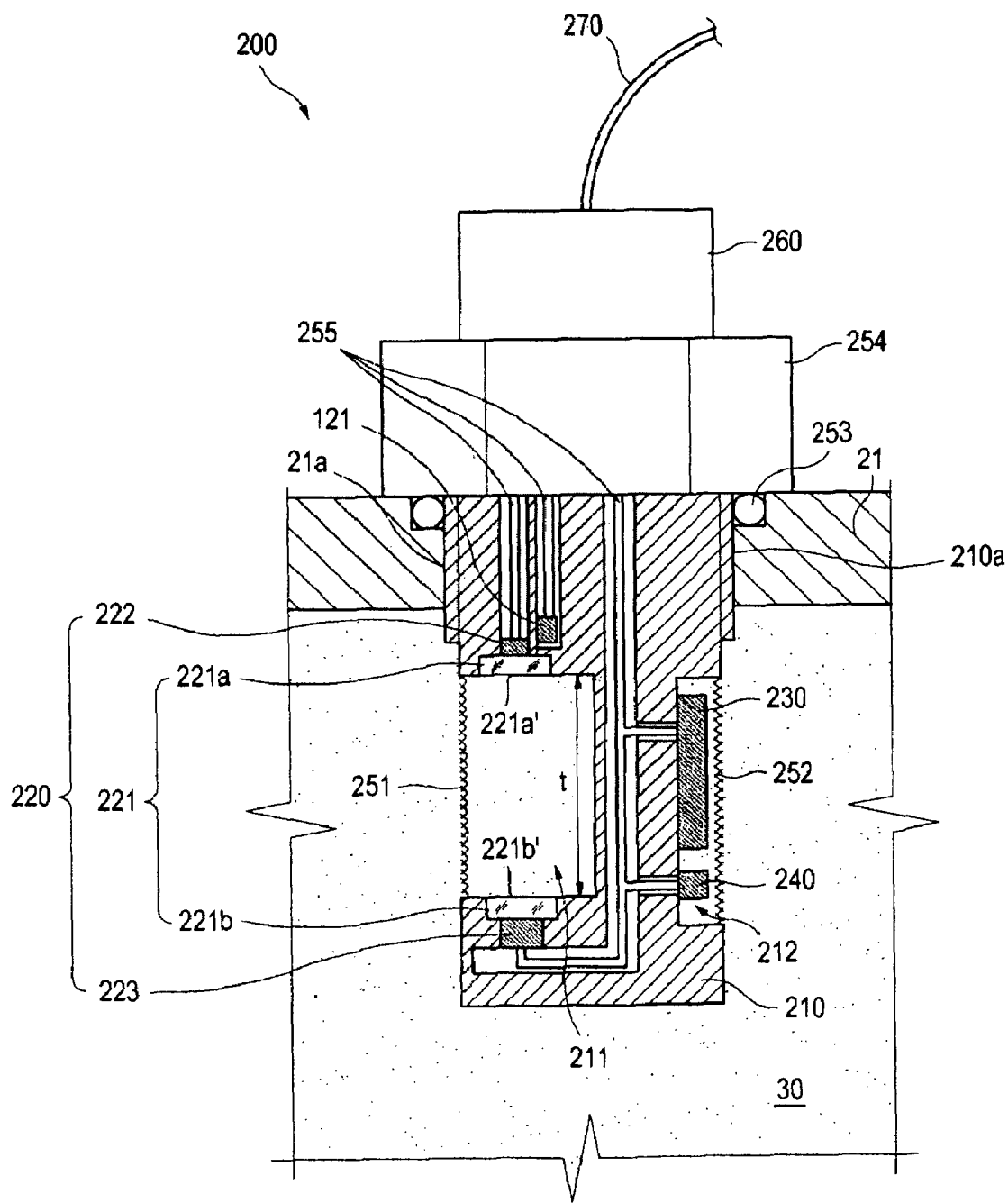
FIG. 2 is a sectional view illustrating a first embodiment of a probe shown in FIG. 1.
Figure 3:
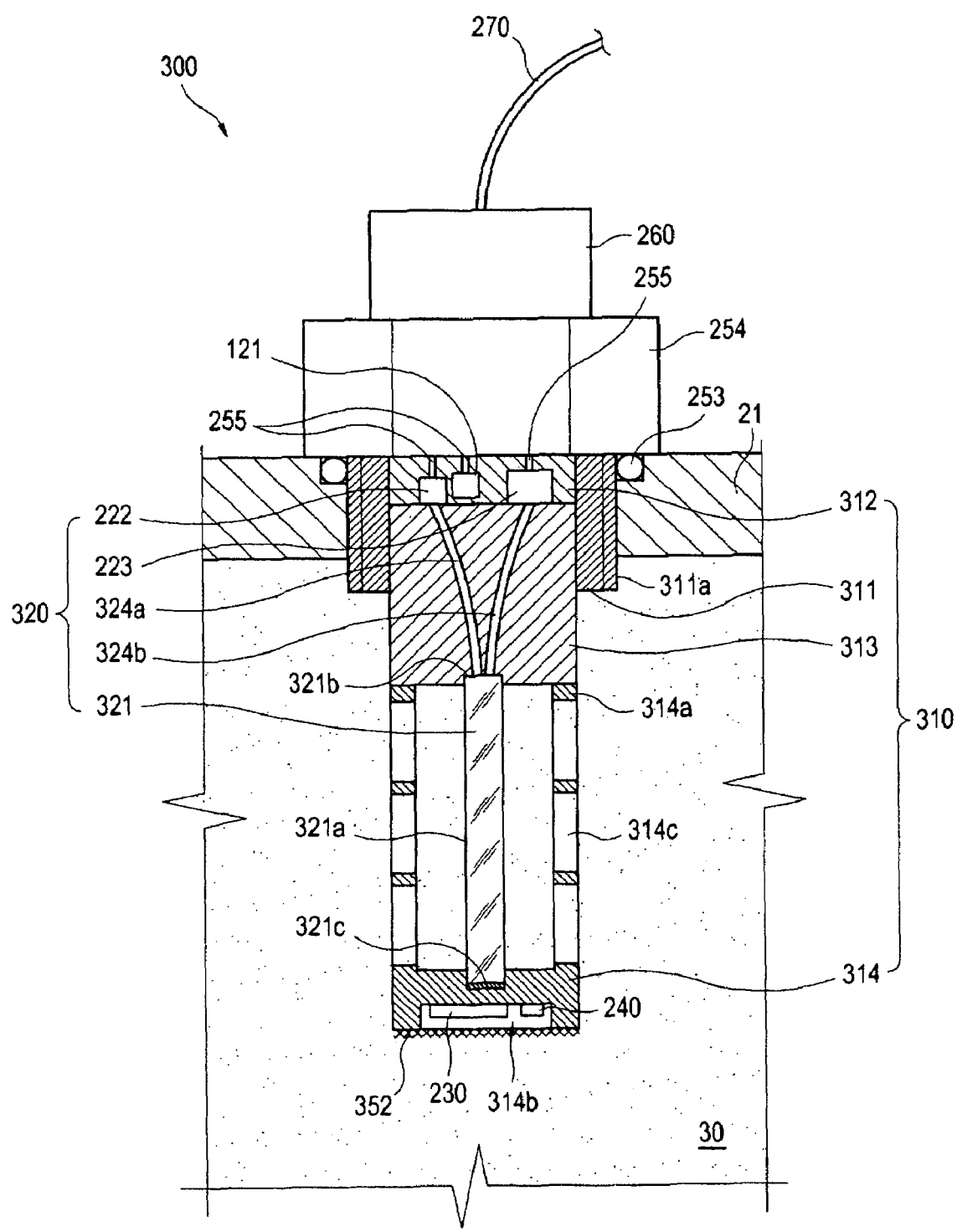
FIG. 3 is a sectional view illustrating a second embodiment of a probe shown in FIG. 1.
Figure 4:
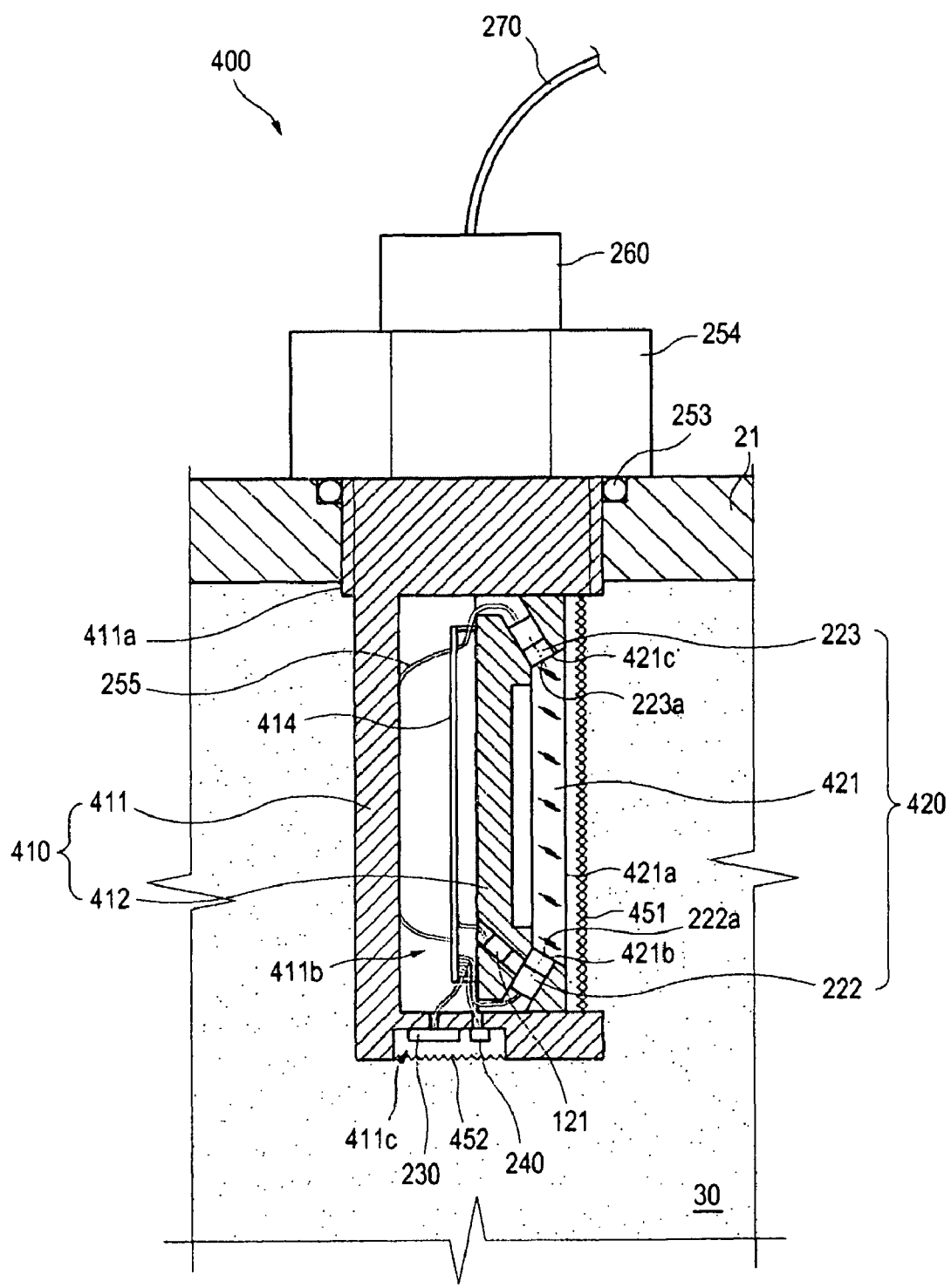
FIG. 4 is a sectional view illustrating a third embodiment of a probe shown in FIG. 1.

FIGS. 2 to 4 show embodiments of the probe which may be equipped to the oil monitoring apparatus of the present disclosure. Probe 200 shown in FIG. 2 may be used for the purposes of monitoring oil having a low light absorption such as hydraulic oil, a transformer oil, a turbine oil, a compressor oil, etc. Probes 300 and 400 shown in FIGS. 3 and 4 respectively may be used for the purposes of monitoring oil having a high light absorption in a visible light waveband such as diesel engine oil.

Referring to FIG. 2, probe 200 may include: a housing 210 for mounting the sensors thereon; first sensor 220 for measuring the chemical deterioration and the total contamination of the oil; second sensor 230 for measuring the water content of the oil; and third sensor 240 for measuring the temperature of the oil.

Housing 210 may be mounted to a member configured to contain the oil (e.g., a wall of the oil tank 21) so as to be in contact with oil 30. Alternatively, if probe 200 is attached to the oil circulation line or the oil circulation pipe, housing 210 may be mounted to such a line or pipe so as to be in contact with the oil thereinside.

Housing 210 may have a first sensor receiving portion 211 and a second sensor receiving portion 212 at a portion of the housing contacting the oil. First sensor 220 may be disposed in the first sensor receiving portion 211, while the second and third sensors 230 and 240 may be disposed in the second receiving portion 212 respectively. Sensor receiving portions 211 and 212 may be configured to be recessed from a surface of housing 210. When probe 200 is installed in oil tank 21 containing oil 30, the oil may be filled into first and second sensor receiving portions 211 and 212.

Housing 210 may have a thread 210a around a portion of its outer periphery. An insertion hole 21a with a thread corresponding to thread 210a may be formed at the oil tank 21. Housing 210 may be threadably-engaged to insertion hole 21a and may be secured to the wall of oil tank 21 through a nut 254. An O-ring 253 or other type of gasket may be disposed between nut 254 and housing 210 to prevent oil leak therebetween.

The oil monitoring apparatus may monitor the conditions of the oil using four parameters (i.e., the chemical deterioration of the oil, the total contamination of the oil, the water content of the oil, and the temperature of the oil). The data for determining those four parameters may be outputted to analyzing module 100 by sensors 220, 230 and 240 of probe 200. Analyzing module 100 may calculate and monitor those four parameters based on the output signals of sensors 220, 230 and 240 to inform a user of the current conditions of the oil in real-time. It may further inform a user of the optimal time for oil exchange intervals and the operative states of the equipment by comparing those parameters with preset threshold values. Herein, the chemical deterioration of the oil may be referred to as a first parameter, the total contamination of the oil may be referred to as a second parameter, the water content of the oil may be referred to as a third parameter, and the temperature of the oil may be referred to as a fourth parameter. Specifically, the first parameter may be defined by chromatic ratio (CR), the second parameter may be defined by total contamination index (TCI), the third parameter may be defined by relative saturation (RS) of the oil by water, and the fourth parameter may be defined by oil temperature (T). The first parameter may indicate the chemical deterioration of the oil. The second parameter may indicate the total contamination of the oil, which is caused by the physical contaminants and the chemical contaminants.

The data for determining the first and second parameters may be obtained from first sensor 220. First sensor 220 may include: an optical passing element 221; light-emitting means 222 for emitting light to optical passing element 222; and color-sensing means 223 for measuring optical intensities of the light passing through optical passing element 221 and outputting signals associated therewith. The light emitted for light-emitting means 222 may pass through the oil by a thickness t and enter color-sensing means 223.

In this embodiment, optical passing element 221 may be comprised of first and second optical windows 221a and 221b. First and second optical windows 221a and 221b may have an interface 221a' and 221b' for contacting oil 30, respectively. First optical window 221a may be disposed at one side of first sensor receiving portion 221, while second optical window 221b may be disposed at the opposite side of first sensor receiving portion 221 so as to be opposed to first optical window 221a. Light-emitting means 222 may contact a face of first optical window 221a, which is opposite to interface 221a'. Color-sensing means 223 may contact a face of second optical window 221b, which is opposite to interface 221b'.

Light-emitting means 222 may be constructed to emit light having spectrums of a red waveband (or wavelength range), a green waveband and a blue waveband (e.g., white light or visible light). The red waveband of the light emitted from light-emitting means 222 may be in the range of from about 590 nm to about 750 nm. Also, the green waveband may be in the range of from about 490 nm to about 610 nm, and the blue waveband may be in the range of from about 400 nm to about 510 nm. Alternatively, light-emitting means 222 may emit such a light in a pulsed manner. The light emitted from light-emitting means 222 may pass through first optical window 221a, oil 30 of the thickness t and second optical window 221b one after another and then enter color-sensing means 223. Color-sensing means 223 may measure each optical intensity of the light having passed through second optical window 221b at each of the red waveband, the green waveband and the blue waveband and may output respective signals corresponding thereto.

The data for determining the third parameter may be obtained from second sensor 230. Further, the data for determining the fourth parameter may be obtained from third sensor 240. Second sensor 230 and third sensor 240 may be disposed in second sensor receiving portion 212 and be attached to the housing by epoxy or other adhesive.

A first sensor receiving portion 211 and second sensor receiving portion 212 may be provided with protective meshes 251 252, respectively, which may protect the sensors situated in the sensor receiving portions against mechanical damages and isolate the sensors from bubbles.

Wires extending from sensors 220, 230 and 240 may be connected to a circuit board (not shown) located in a cover part 260 coupled to one side of housing 210. A wire 270 may extend from cover part 260 and may be connected to analyzing module 100. Light-emitting means 222, color-sensing means 223, second sensor 230 and third sensor 240 may be connected to a PCB with a preamplifier mounted therein via a wire 255. The PCB may be located in cover part 260.

In probe 200 for monitoring oil having a low light absorption shown in FIG. 2, first sensor 220 may measure the optical intensity of the light passing through the oil of the measurement thickness t. Typically, in monitoring oil having a high light absorption (e.g., diesel oil), if the measurement thickness through which light passes is substantially thick, then the emitted light may be absorbed in large quantities causing some difficulty in precisely measuring its optical intensity. It is also difficult to have a very small measurement thickness to avoid such a problem, in view of fabrication issues. Even if it can be made small, there is the additional problem of the oil not easily entering the narrow measurement thickness. Accordingly, in monitoring oil having a high optical absorption, there is a need to form a consecutive small measurement thicknesses to enhance precision of the measurement. In this regard, in this embodiment, the probe for monitoring the oil having a high light absorption at a visible light waveband may utilize a total internal reflection (TIR) technique. This allows measuring an optical ray, which passes through thin oil layers for measurement while undergoing the total internal reflection.

FIG. 3 is a schematic sectional view of the probe 300 for monitoring the oil having a high light absorption in a visible light waveband (e.g., diesel oil). In FIG. 3, like reference numerals refer to like elements in comparison with the probe 200 of the first embodiment.

Referring to FIG. 3, probe 300 may include: a housing 310 for mounting the sensors thereon, housing 310 being mounted to a wall of oil tank 21 so as to be in contact with the oil; a first sensor 320 for measuring the chemical deterioration and the total contamination of the oil; second sensor 230 for measuring the water content of the oil; and third sensor 240 for measuring the temperature of the oil.

Housing 310 may include: a fixing portion 311 with a thread 311a for fixation to the oil tank 21; an insertion portion 312 inserted in fixing portion 311 for situating the light-emitting means and the color-sensing means therein; a bush portion 313 contacted to insertion portion 312 in fixing portion 311 for disposing optical fibers therein; and a hollow portion 314 for disposing an optical passing element therein. One end of hollow portion 314 may be contacted to bush portion 313, while the opposite end thereof may become a free end. A plurality of through-holes 314c may be formed through hollow portion 314 such that oil 30 flows in and out therethrough.

First sensor 320 may include: optical passing element 321 along which a light passes through the oil of a predetermined thickness; light-emitting means 222 for emitting the light to optical passing element 321; color-sensing means 223 for measuring the optical intensities of the light having passed through optical passing element 321 and outputting signals associated therewith; a first optical fiber 324a for optically connecting optical passing element 321 and light-emitting means 222; and a second optical fiber 324b for optically connecting optical passing element 321 and color-sensing means 223.

Optical passing element 321 may have an interface 321a for contacting to oil 30. Optical passing element 321 may have a cylindrical shape and may be made from optical glass having refractive index higher than that of oil 30 (particularly, borosilicate glass BK8). One end of the optical passing element 321 may be brought into contact with first and second optical fibers 324a, 324b a in bush portion 313. The opposite end of optical passing element 321 may be coupled to an inner wall surface of hollow portion 314. The one end of optical passing element 321 may be optically transparent. Optical passing element 321 may be positioned such that it is optically connected to bifurcated first and second optical fibers 324a, 324b at its one end. The opposite end of optical passing element 321c may be coated with a light-reflection member. When probe 300 is installed to oil tank 21, oil 30 comes into contact with interface 321a of the optical passing element through through-holes 314c of the hollow portion.

First optical fiber 324a may be connected to the one end 321b of the optical passing element at its one end and to light-emitting means 222 at its other end. Second optical fiber 324b may be connected to one end 321b of the optical passing element at its one end and to color-sensing means 223 at its other end. The light emitted from light-emitting means 222 may pass through first optical fiber 324a and then enters optical passing element 321. The incident light may pass through optical passing element 321 while totally reflecting at interface 321a of optical passing element 321. While the incident light totally reflects at interface 321a, a certain amount of the light infiltrates into the oil and is then absorbed thereinto. Thus, the optical intensity of the light, which totally reflects at interface 321a, is decreased. The incident light reflects at opposite end 321c of the optical passing element and then passes while totally reflecting again, to enter color-sensing means 223 through one end 321b of optical passing element 321 via second optical fiber 324b.

Optical passing element 321 may have a suitable ratio of diameter to length so that optical attenuation effects can be accumulated. Preferably, optical passing element 321 may have a ratio of diameter to length equal to or higher than 10 such that the incident light can totally reflect more than three times.

Second sensor 230 and third sensor 240 may be disposed in a sensor receiving portion 314b formed at the opposite end of hollow housing 314. A sensor receiving portion 314b may be provided with a protective mesh 352, which may protect second sensor 230 and third sensor 240 against mechanical damages and isolate them from bubbles.

FIG. 4 shows another probe 400 for monitoring oil having a high light absorption at a visible light waveband (e.g., diesel oil). In FIG. 4, like reference numerals refer to like elements in comparison with probe 200 of the first embodiment and probe 300 of the second embodiment.

Referring to FIG. 4, probe 400 may include: a housing 410 for mounting sensors thereon, housing 410 being mounted to a wall of oil tank 21 so as to be in contact with oil 30; a first sensor 420 for measuring the chemical deterioration and the total contamination of the oil; second sensor 230 for measuring the water content of the oil; and third sensor 240 for measuring the temperature of the oil.

Housing 410 may include: a fixing portion 411 with a thread 411a for fixation to oil tank 21; and an insert 412, which is fixed to fixing portion 411, and in which first sensor 420 is disposed. Insert 412 may be inserted in a first sensor receiving portion 411b formed at fixing portion 411 and is fixed thereto. Fixing portion 411 may have a second sensor receiving portion 411c for disposing second and third sensors 230, 240 therein at its opposite end.

First sensor 420 may include: an optical passing element 421 along which a light passes through the oil of a predetermined thickness; light-emitting means 222 for emitting the light to optical passing element 421; and color-sensing means 223 for measuring the optical intensities of the light having passed through optical passing element 421 and outputting signals associated therewith.

Optical passing element 421 may have a hexahedral or polyhedral shape. Optical passing element 421 may be made from optical glass having a refractive index higher than that of oil 30 (e.g., N-SF6 (n=1.81) from SCHOTT GLASS). One face of optical passing element 421 may comprise an interface 421a for contacting to oil 30. Optical passing element 421 may have a light-incident face 421b and a light-outgoing face 421c. Preferably, a ratio of length to thickness of optical passing element 421 may be equal to or higher than 10 to provide the total internal reflection three times or more.

Light-incident face 421b of optical passing element 421 may be chamfered off with respect to interface 421a such that it lies perpendicularly to an optical axis 222a of the light emitted from light-emitting means 222. Light-outgoing face 421c of optical passing element 421 may be chamfered off with respect to interface 421a such that it lies perpendicularly to an optical axis 223a of light entering the color-sensing means 223. Chamfered light-incident face 421b and chamfered light-outgoing face 421c may be formed so as to satisfy the condition of the total internal reflection.

Second sensor 230 and third sensor 240 may be disposed in second sensor receiving portion 411c and are attached thereto by epoxy or another adhesive.

At first and second sensor receiving portions 411b, 411c protective meshes 451 and 452 may be provided respectively, which may protect the sensors situated in the sensor receiving portions against mechanical damages and isolate the sensors from bubbles.

Wires extending from the sensors may be connected to analyzing module 100 via a plate 414 fixed to insert 412 and a cover 260.

Figure 5:
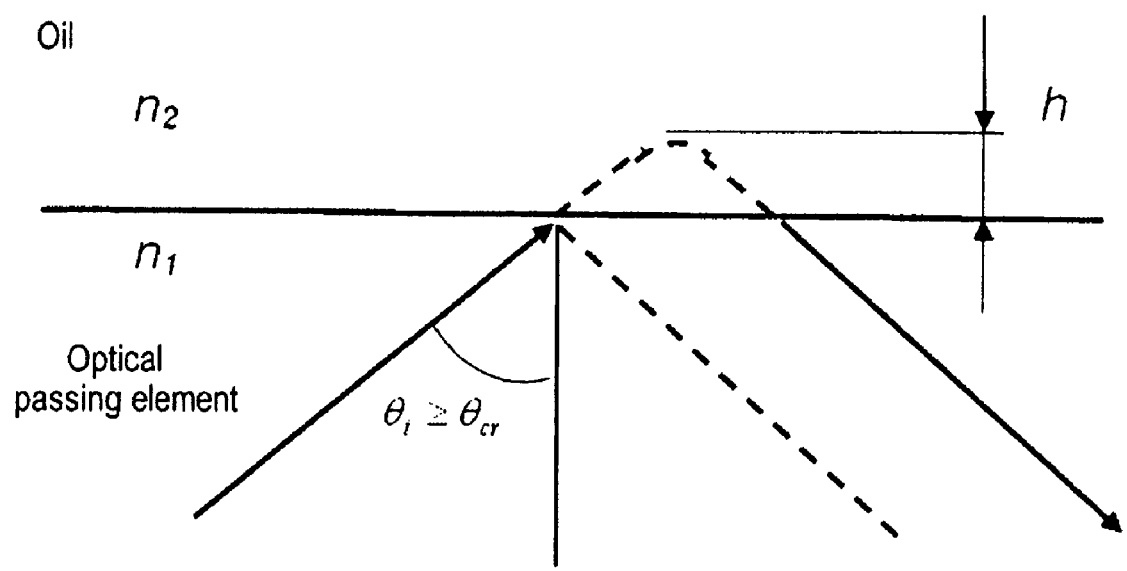
FIG. 5 illustrates total internal reflection within an optical passing element.

FIG. 5 illustrates the total internal reflection in probes 300 or 400 shown in FIGS. 3 and 4.

In probe 300 or 400, the optical light ray emitted from the light-emitting means 222 may be incident on the interface between optical passing element 321, 421 (i.e., cylindrical optical passing element 321 or hexahedral optical passing element 421, which is made from optical glass having a refractive index of $n_1$) and the oil (i.e., an external medium having a refractive index of $n_2$). In such a case, when an incident angle θi of the incident light may exceed a critical angle θcr of the total internal reflection, as can be seen from the following Equation (1), the optical light ray may pass through the optical passing element without substantial loss of power while undergoing the total internal reflection.

$$\theta_i \geq \theta_{cr} = \arcsin(n_2/n_1) \quad \text{Eq. (1)}$$

The losses of radiation during the total internal reflection may take place due to the absorption in the optical passing element medium and the penetration into the external medium (i.e., oil). In the total internal reflection, the incident light may penetrate into the external medium (i.e., oil) by a depth h. The penetration depth h may be calculated by the following Equation (2). For instance, it may be about 1 μm.

$$h = \frac{\lambda}{n_1^2} \cdot 2\pi \cdot (n_1^2 \cdot \sin^2\theta_t - n_2^2)^{1/2} \quad \text{Eq. (2)}$$

wherein λ is an optical wavelength of the incident light.

As shown in the following Equation (3), a total length t (i.e., measurement thickness of oil), by which the light passing through the optical passing element penetrates into the oil, may be a product of the double depth h and the number k of the reflections which may occur at the interface between the oil and the optical passing element.

$$t \approx 2hk \quad \text{Eq. (3)}$$

In probes 200, 300, 400 of the oil monitoring apparatus according to the present disclosure, light-emitting means 222 may include, but is not limited to, a RGB LED such as B5-4RGB-CBA from Roithner Lasertechnik, or a white LED from Marl Optosource Co. Color-sensing means 223 may include, but is not limited to, a color sensor (particularly, a 3-component color sensor) such as MCS3AT/BT from MAZeT Gmbh or TCS230 from Texas advanced optoelectronic solutions Inc.

In embodiments of the present disclosure, the light, which may be emitted from light-emitting means 22 (particularly, the RGB LED or the white LED) to pass through the oil with the measurement thickness t, may be incident to color-sensing means 223 (particularly, the color sensor), which may measure optical intensities at three wavebands (i.e., red, green and blue wavebands). Color-sensing means 223 may measure respective optical intensities at those three wavebands and output signals associated therewith to a processor 111 of a control unit 110 (see FIG. 6). Processor 111 may calculate the above-described four parameters.

The calculation of the first to fourth parameters will be described below.

The first parameter may be associated with the oxidative and thermal deterioration of the oil. First sensor 220, 320, 420 may measure the optical intensities at each of the red, green and blue wavebands from the light that passes through the oil after being emitted from light-emitting means 222.

Korean Patent No. 10-0795373 discloses a technology which measures chromatic ratio (CR) as a parameter associated with oxidative and thermal deterioration of oil and measures change in optical intensities of oil at three wavebands as a parameter associated with total contamination of oil. As for mineral oil, it is known in the art that the intensity in optical spectrum of the light passing through the oil becomes strong at a longer waveband with the progress of the oxidative and thermal deterioration of the oil.

The first parameter, which may be defined by the chromatic ratio, may be a ratio of the optical intensity at the red waveband to that at the green waveband of the light having passed through the oil. The chromatic ratio may be determined using the output $U_R$ at the red waveband and the output $U_G$ at the green waveband from the color-sensing means, as shown in the following Equation (4).

$$CR = \frac{U_R}{U_G} \quad \text{Eq. (4)}$$

Such chromatic ratio parameter may become high as an oil service time becomes longer. That is, as the optical intensity at the red waveband of the light passing through the oil becomes larger than the optical intensity at the green waveband with the progression of the chemical deterioration of the oil, the output $U_R$ in the red waveband of the color-sensing means may become larger than the output $U_G$ in the green waveband.

The total contamination of the oil may depend on the content of oxidation and aging products, contaminating dust, wear debris, air bubbles and etc. in the oil. The second parameter associated with the total contamination of the oil may be evaluated by comparing the change in optical intensity of used oil with that of fresh oil. The second parameter may be defined by a total contamination index (TCI) at said three wavebands. The TCI may be evaluated as the changes in optical intensity at said three wavebands (i.e., red ($\Delta D_R$), green ($\Delta D_G$) and blue ($\Delta D_B$)) as shown in the following Equations (5), (6) and (7).

$$TCI_R = \Delta D_R = D_{R,used} - D_{R,fresh} = \ln\frac{U_{R,fresh}}{U_{R,used}} \quad \text{Eq. (5)}$$

$$TCI_G = \Delta D_G = D_{G,used} - D_{G,fresh} = \ln\frac{U_{G,fresh}}{U_{G,used}} \quad \text{Eq. (6)}$$

-continued $$TCI_B = \Delta D_B = D_{B,used} - D_{B,fresh} = \ln\frac{U_{B,fresh}}{U_{B,used}} \quad \text{Eq. (7)}$$

In the above Equations 5 to 7, $D_{R,fresh}$, $D_{G,fresh}$ and $D_{B,fresh}$ denote the optical intensities of the fresh oil at the red, green and blue wavebands respectively, while $D_{R,used}$, $D_{G,used}$ and $D_{B,used}$ denote the optical densities of the used oil at the red, green and blue wavebands respectively. $U_{R,fresh}$, $U_{G,fresh}$ and $U_{B,fresh}$ denote the output signals at the red, green and blue wavebands respectively in the fresh oil test, while $U_{R,used}$, $U_{G,used}$ and $U_{B,used}$ denote the output signals at the red, green and blue wavebands respectively in the used oil test.

Meanwhile, the Equation (2) shows that the penetration depth h depends on the wavelength λ. This fact should be taken into account in design of probes 300, 400 using the TIR technique. Thus, normalization to a unified penetration depth h (particularly, to the penetration depth of the light at the red waveband) may be performed.

The TCI in the i-th (i.e., red, green and blue) waveband may be determined as the change in optical intensity $\Delta D_i$ as shown in the following Equation (8).

$$\Delta D_i = \ln\left(\frac{U_{i,fresh}}{U_i}\right) = \ln\left(\frac{A_i \cdot e^{-\lambda_i 2k\alpha_{i,0}}}{A_i \cdot e^{-\lambda_i 2k\alpha_i}}\right) = -\lambda_i \cdot 2 \cdot k \cdot (\alpha_{i,0} - \alpha_i) \quad \text{Eq. (8)}$$

wherein $\alpha_{i,0}$ and $\alpha_i$ are an absorption coefficient of the fresh oil and the used oil in the i-th waveband, $A_i$ is an optical intensity of the white LED in the i-th waveband, and k is the number of the light reflections occurring between the oil and the interface of the optical passing element.

In case the white LED is applied as the light-emitting means and the MCS3AT is applied as the color-sensing means, an average wavelength of the red waveband may be about 640 nm, that of the green waveband may be 560 nm and that of the blue waveband may be about 460 nm.

To normalize the optical intensities to the penetration depth of the red waveband (i.e., to depth $h = k \cdot \lambda_R$), in the case of the TCI at the green waveband, the optical intensity at the green waveband $D_G$ may be multiplied by a ratio of $640/560 = 1.14$ and, in the case of the TCI at the blue waveband, the optical intensity at the blue waveband $D_B$ may be multiplied by a ratio $640/460 = 1.39$.

$$TCI_R = \Delta D_R \quad \text{Eq. (9)}$$

$$TCI_G = \Delta D_{G,norm} = \Delta D_G \cdot 1.14 \quad \text{Eq. (10)}$$

$$TCI_B = \Delta D_{B,norm} = \Delta D_B \cdot 1.39 \quad \text{Eq. (11)}$$

In the course of the CR calculation in probes 300 or 400 using the total internal reflection technique, the normalization of the measured outputs in the green and blue wavebands may be performed by employing relative values as follows. The measured outputs in the green and red wavebands may be as the following Equations (12) and (13).

$$U_{G,fresh} = S_G \cdot A_G \cdot e^{-\lambda_G k\alpha_{G,0}}$$

$$U_G = S_G \cdot A_G \cdot e^{-\lambda_G k\alpha_G} \quad \text{Eq. (12)}$$

$$U_{R,fresh} = S_R \cdot A_R \cdot e^{-\lambda_R k\alpha_{R,0}}$$

$$U_R = S_R \cdot A_R \cdot e^{-\lambda_R k\alpha_R} \quad \text{Eq. (13)}$$

wherein $S_G$ and $S_R$ are sensitivities of the color-sensing means in the green and red wavebands, $U_{G,fresh}$ and $U_{R,fresh}$ are outputs from the fresh oil and $U_G$ and $U_R$ are outputs from the used oil.

Relative change of the outputs in the used oil outputs to the outputs in the fresh oil outputs may be as the follow Equation (14).

$$U_G^* = \frac{U_G}{U_{G,fresh}} = e^{-\lambda_G k(\alpha_G - \alpha_{G,0})} \quad \text{Eq. (14)}$$

$$U_R^* = \frac{U_R}{U_{R,fresh}} = e^{-\lambda_R k(\alpha_R - \alpha_{R,0})} = e^{-h(\alpha_R - \alpha_{R,0})}$$

The relative output in the green waveband, which is normalized to the penetration depth h, may be as the following Equation (15).

$$U_{G,norm}^* = \left(\frac{U_G}{U_{G,fresh}}\right)_{norm} \quad \text{Eq. (15)}$$

$$= e^{-\lambda_G k(\alpha_G - \alpha_{G,0}) \cdot 1.14}$$

$$= \left(\frac{U_G}{U_{G,fresh}}\right)^{1.14}$$

$$= (U_G^*)^{1.14}$$

Thus, in the case employing the probes 300 or 400 using the TIR technique, the CR may be defined as a ratio of the relative output in the red waveband to the normalized relative output in the green waveband, as shown in the following Equation (16).

$$CR = \frac{U_R^*}{U_{G,norm}^*} \quad \text{Eq. (16)}$$

Second sensor 230, which may be mounted to housing 210, 310 or 410, may include, but is not limited to, an air humidity sensor (e.g., HIH-3610 from Honeywell Inc.). Such a sensor may use a thermoset polymer, three layer capacitance construction and silicon-integrated platinum electrodes of an on-chip type. Output signal of such a sensor may be voltage (U). In order to calculate the relative saturation (RS), the following Equation (17) may be used.

$$U = U_{supply} \cdot (0.0062 \cdot RS_s + 0.16) \text{ at } 25° \text{ C.} \quad \text{Eq. (17)}$$

wherein $U_{supply}$ is a supplied voltage.

The output of all absorption-based humidity sensors (e.g., capacitive, bulk resistive, conductive film, etc.) may be affected by temperature. For this reason, temperature compensation may be applied using the following Equation (18).

$$RS = \frac{RS_s}{1.0546 - 0.00216 \cdot T} \quad \text{Eq. (18)}$$

wherein RS is a true relative saturation and T is temperature in ° C.

Based on the Equations (17) and (18), control unit 110 may calculate the water content in oil with percentage as the RS parameter (i.e., the third parameter) and outputs the result thereof.

While such an air humidity sensor has a protective polymer layer, it is unsuitable to be used as an oil moisture sensor. The Honeywell data shows the results of chemical resistivity test of such an air humidity sensor. It is clear from said data that such an air humidity sensor needs additional protection against contamination caused by oil. Accordingly, in certain embodiments, in order to solve such a problem, an oleophobic coating may be additionally applied on the protective layer of the existing HIH-3610 air humidity sensor. Particularly, Novec Coating EGC-1720 (3M Co.), which is clear and low viscosity solution of a fluorosilane polymer carried in a hydrofluoroether solvent, may be used for the additional coating.

Third sensor 240, which is mounted to probes 200, 300 or 400, may serve to determine the temperature of the oil. Third sensor 240 may include, but is not limited to, a Temperature-to-Voltage Converter (e.g., TC1047 from Microchip). The TC1047 is a linear voltage output temperature sensor, the output voltage of which is directly proportional to the measured temperature. The TC1047 may measure temperature ranging from −40° C. to 125° C. The output voltage U may vary along with temperature change T as shown in the following Equation (19).

$$U[mV] = 10\left[\frac{mV}{°C.}\right] \cdot T[°C.] + 500[mV] \qquad \text{Eq. (19)}$$

Control unit 110 may calculate the oil temperature in centigrade degrees and outputs the result thereof.

Figure 6:
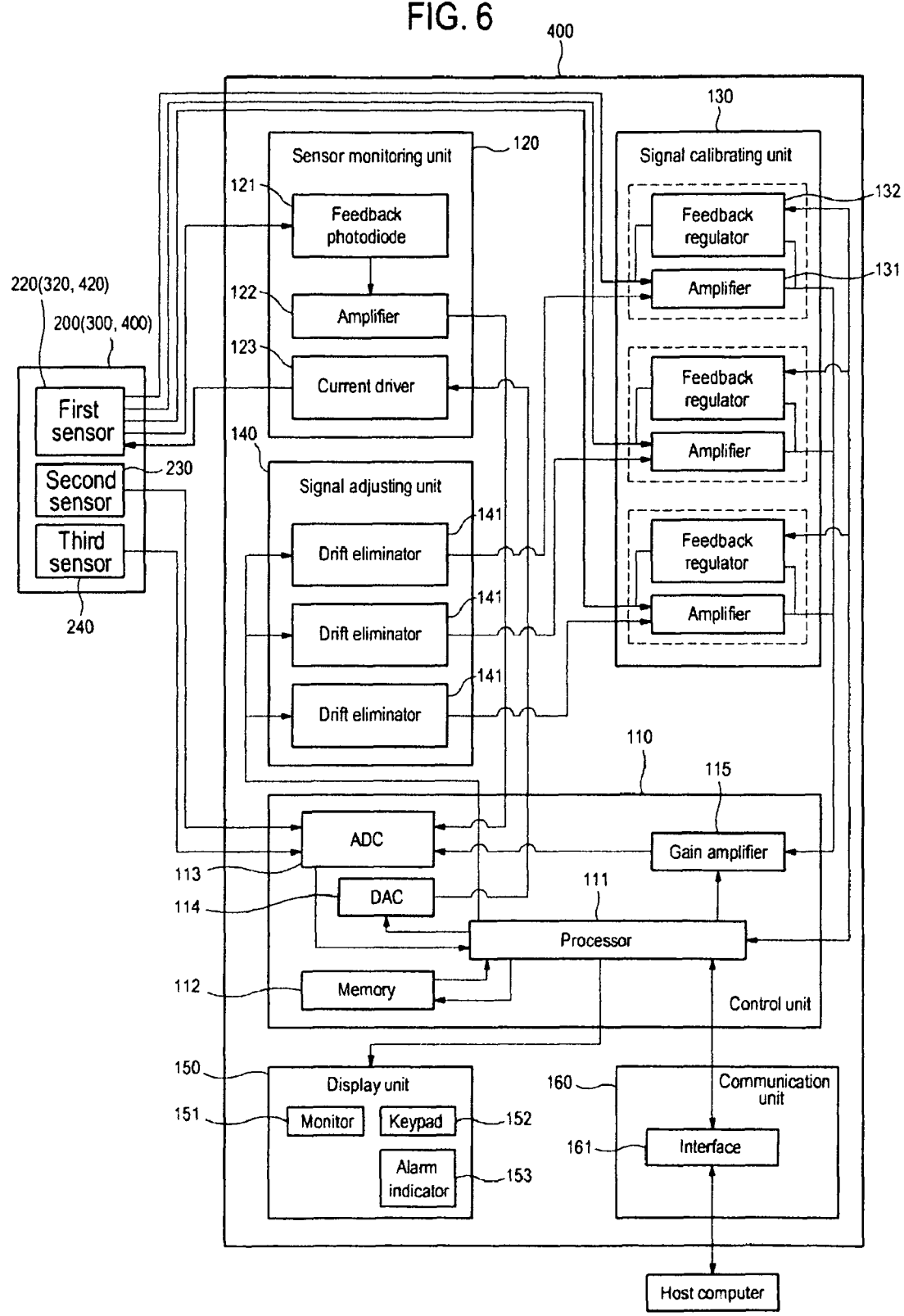
FIG. 6 is a schematic block diagram showing an illustrative embodiment of an analyzing module.

Analyzing module 100 will be described in detail with reference to FIGS. 1 and 6.

Analyzing module 100 may include control unit 110, a sensor monitoring unit 120, a signal calibrating unit 130, a signal adjusting unit 140, a display unit 150 and a communication unit 160.

Control unit 110 may perform control on general operations of oil monitoring apparatus 10. Control unit 110 may include processor 111, a memory 112, an ADC 113, a DAC 114 and a programmable gain amplifier 115.

Processor 111 may control operations of probes 200, 300, 400. Processor 111 may be pre-programmed so as to process the output signals of the sensors for calculating the chromatic ratio (the first parameter), the total contamination index (the second parameter), the relative saturation of oil by water (the third parameter) and the oil temperature (the fourth parameter). Further, the processor 111 may control sensor monitoring unit 120, signal calibrating unit 130 and signal adjusting unit 140 and sends data to display unit 150 and communication unit 160 through hardware interface.

Memory 112 may serve to store program codes for carrying out oil condition measurement in real time, which are executed by the processor 111. Memory 112 may be used to store initial information on the fresh oil or operational parameters such as oil oxidation and total contamination parameters of the fresh oil, nominal water content, lubricant temperature, etc. Further, memory 112 may contain threshold values of measured parameters so as to determine suitability of the oil to be analyzed.

Sensor monitoring unit 120 may monitor optical radiation levels of light-emitting means 222. Sensor monitoring unit 120 may include a feedback photodiode 121 (see FIGS. 2 to 4), an amplifier 122 and a current driver 123. Feedback photodiode 121 may serve as means for measuring optical radiation, which measures the optical radiation levels of light-emitting means 222 and outputs signals, for purposes of feedback control for equalizing the optical intensities of light-emitting means 222. Sensor monitoring unit 120 may increase current to increase the optical intensities when the intensities of the light radiated from light-emitting means 222 are weak. When the intensities are strong, sensor monitoring unit 120 may decrease current to equalize the intensities of the light radiated from light-emitting means 222. Feedback photodiode 121 may be positioned adjacent to light-emitting means 222 of probe 200, 300 or 400. A silicon photodiode (more particularly, photodiode SP-1ML from Kondenshi Corp.) may be used as the feedback photodiode 121. The optical radiation of light-emitting means 222 may be measured by feedback photodiode 121. The output signals of feedback photodiode 121 may enter the processor 111 via amplifier 122 and ADC 113. Processor 111 may compare those output signals with the initial value stored in memory 112 and then feeds a result signal associated therewith to a current driver of light-emitting means 222 of probe 200, 300 or 400 through DAC 114.

Signal calibrating unit 130 may include three amplifiers 131 and three programmable feedback regulators 132. Signal calibrating unit 130 may calibrate sensitivities of first sensors 220, 320 or 420, thereby allowing oil having different grades and oil being in a wide range of contamination level to be tested. To this end, it the output signals of color-sensing means 223 should be calibrated so that they can remain between a minimal level (e.g., 1000 mV) and a maximal level (e.g., 200 mV) of a pre-set value. When the output signals of color-sensing means 223 from the oil to be tested are too weak or too strong, feedback regulator 132 may be operated by processor 111 and therefore a final output signal may be automatically adjusted such that it can be in a range of the minimal level from about 1000 mV to the maximal level of about 2000 mV. Accordingly, various oils in wide contamination levels can be tested. The calibration technique may be as follows. The output signals of color-sensing means 223 may enter amplifiers 131 of signal calibrating unit 130 at the time of each light pulse of light-emitting means 222. The output signal of amplifier 131 may enter processor 111 via programmable gain amplifier 115 and ADC 113. The signal value may be compared with the minimal and maximal levels of the preset critical value at processor 111. If the signal value is less or higher than the minimal and maximal levels of the critical value, then a gain of programmable gain amplifier 115 may be correspondingly increased or decreased. To adjust the output signal into the range between the levels of the pre-set value, a programmable feedback regulator based on digital potentiometer (e.g., Single Digital Potentiometer MCP41100 with SPI interface from Microchip Technology Inc.) may be additionally applied. The programmable feedback regulator may be controlled by processor 111. When the output signals are between the minimal and maximal levels of the critical value, the first parameter of the chromatic ratio and the second parameter of the total contamination indexes may be calculated and results therefrom may be outputted.

Signal adjusting unit 140 may include three drift eliminators 141. Signal adjusting unit 140 may adjust outputs so as to eliminate drift (shift) of "zero levels" of signals caused by temperature instability, ambient light and other effects. The adjustment may be performed as follows. The outputs of color-sensing means 223 at the respective R, G and B wavebands may be measured at time period between the light pulses of light-emitting means 222. The measured outputs may be compared with prescribed zero levels for three channels (R, G and B). The difference therebetween may be adjusted to null by drift eliminators 141. Digital potentiometers (more particularly, Single Digital Potentiometer MCP41100 with SPI interface, Microchip Technology Inc.), which are controlled by control unit 110 according to software, may be used as drift eliminator 141.

Analyzing module 100 may further include display unit 150 for displaying information relating to the condition of the oil. Display unit 150 may include a monitor 151 and an operator input detector. A Liquid Crystal Display (LCD) may be used as monitor 151, but is not limited thereto. Monitor 151 may function to show the four parameters produced by calculating data obtained via probe 200, 300 or 400. Particularly, monitor 151 may present a set of oil condition parameters such as the chromatic ratio, the water content, the total contamination indexes at three R, G and B wavebands and the oil temperature. The operator input detector may include a keypad 152, which enables a user to input data, information, function commands, etc. Keypad 152 may include three key buttons comprised of the following: a "Reset" button serving to interrupt and restart software execution; a "Save Data" button configured to be pushed in order to write a data of oil to memory when a user plans to employ reference data such as fresh oil data; and a "Reference Data" button allowing user to read the data from the memory. Display unit 150 may further include an alarm indicator 153 for indicating alarm when the oil reaches any critical conditions. Alarm indicator 153 may include one or more light-emitting diodes (LEDs). For example, alarm indicator 153 may include a tri-state LED displaying green, yellow or red colors depending on the health state of the lubricant.

Analyzing module 100 may further include communication unit 160 for communication with a host computer. Communication unit 160 may include an interface 161 for communicating commands and parameter information between processor 111 and host computer. Interface 161 may be comprised of a hardware wire interface (e.g., RS-232 or USB standard)) or a hardware wireless interface (e.g., an interface including a radio transmitter, a radio receiver and an antenna). The wireless interface may eliminate costs, noise problems and other problems related with the wire interface. The data may be transmitted to the host computer to perform time-based trending and analysis to thereby determine oil condition, full equipment condition and optimal oil exchange interval. Meanwhile, analyzing module 100 may be constructed without the host computer. In such a case, all processing including data analyses may be accomplished by the processor and be displayed by display unit 150.

Figure 7:
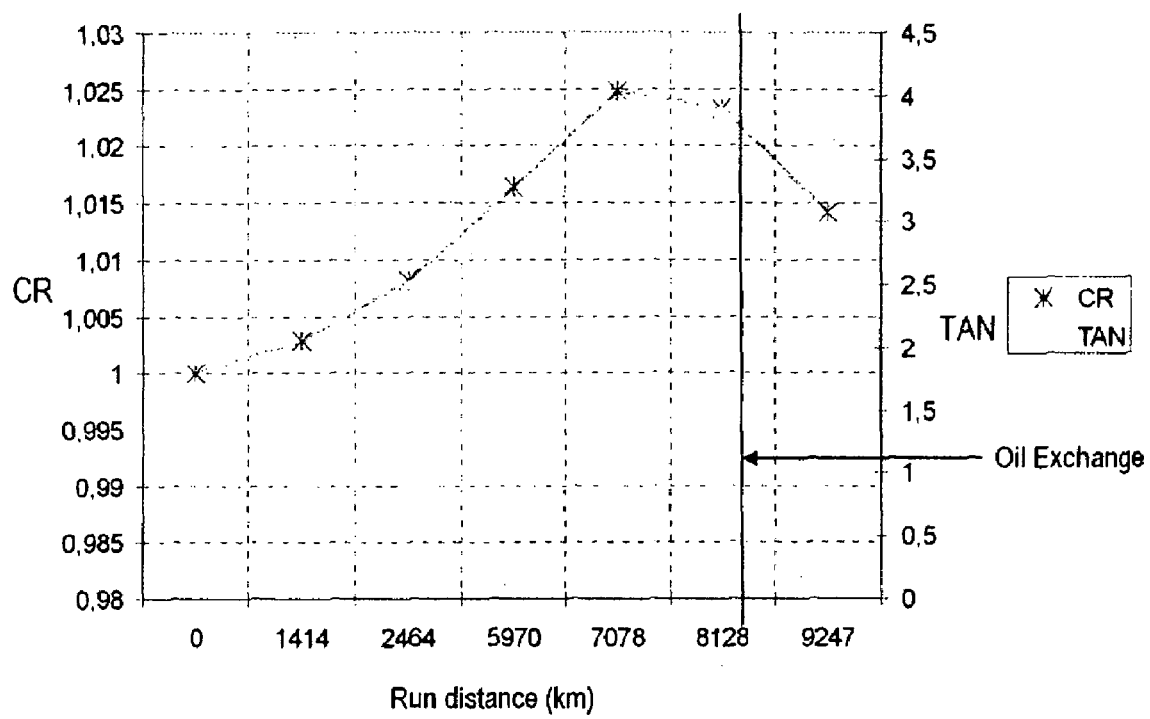
FIG. 7 is a diagram illustrating output signals of an oil monitoring apparatus.

An operating algorithm of one embodiment of the apparatus for integrated in-line oil monitoring according to the present disclosure will be described below. FIG. 7 shows the output signals according to the algorithm.

The algorithm may include following steps.

Step 1. When the oil monitoring apparatus 10 is switched on, program may start and input data may be initialized. Light-emitting means 222 may be not energized.

Step 2. Three outputs $U_R$, $U_G$, $U_B$ (in the R, G and B wavebands) of probe 200, 300, 400 may be read. The drifts may be calculated as differences between the outputs and the prescribed "zero level" value $U_0$. ($U_{R\_drift}=U_R-U_0$; $U_{G\_drift}=U_G-U_0$; $U_{B\_drift}=U_B-U_0$). Processor 111 may control a variation in resistance of the digital potentiometers of signal adjusting unit 140 while the drifts are eliminated. Besides, the output of feedback photodiode 121 may be read as $U'_F$.

Step 3. Light-emitting means 222 may be energized and the output of feedback photodiode 121 of the sensor monitoring unit 120 may be read as $U''_F$. A value of $U''_F-U'_F$ may be calculated and compared with prescribed $U_F$. The value $U'_F$ may be adjusted by a fed voltage under the control of the processor 111 while $(U''_F-U'_F)=U_F$.

Step 4. Outputs $U_R$, $U_G$, $U_B$ of color-sensing means may be read and a maximal value $U_{max}$ may be found from $U_R$, $U_G$, $U_B$.

A) If this maximal value is exterior to prescribed range $\Delta U_{max}$, then a resistance of the digital potentiometer of programmable feedback regulator 131 of signal calibrating unit 130 may be adjusted under the control of processor 111 while $U_{max}$ belongs to the range $\Delta U_{max}$. Light-emitting means 222 may be de-energized and Steps 2-3 may be repeated to verify all installation-specific settings.

B) If this maximal value is within the prescribed range $\Delta U_{max}$, then outputs $U_R$, $U_G$, $U_B$ of color-sensing means 223 may be accumulated and the number of reading i may be increased by 1. Then, light-emitting means 222 may be de-energized and the outputs $U_{RS}$ of second sensor 230 and the outputs $U_T$ of third sensor 240 may be read and the outputs $U_R$, $U_G$, $U_B$, $U_{RS}$, $U_T$ may be sent to the host computer. Steps 2-4 may be repeated while the number of reading becomes 127.

Step 5. Calculation of average values of $U_R$, $U_G$, $U_B$, $U_{RS}$ and $U_T$ obtained by 128 readings may be performed. By using the average values, the first parameter (CR), the second parameter (TCI), the third parameter (RS) and the fourth parameter (T) may be calculated according to the above Equations 4-7, 9-11 and 13-15.

Step 6. The first to fourth parameters may be displayed.

Step 7. The measured parameters may be compared with the prescribed threshold values and decision on the oil condition and the equipment condition may be made.

Step 8. The oil condition and the equipment condition may be outputted through alarm indicator 153.

Figure 8:
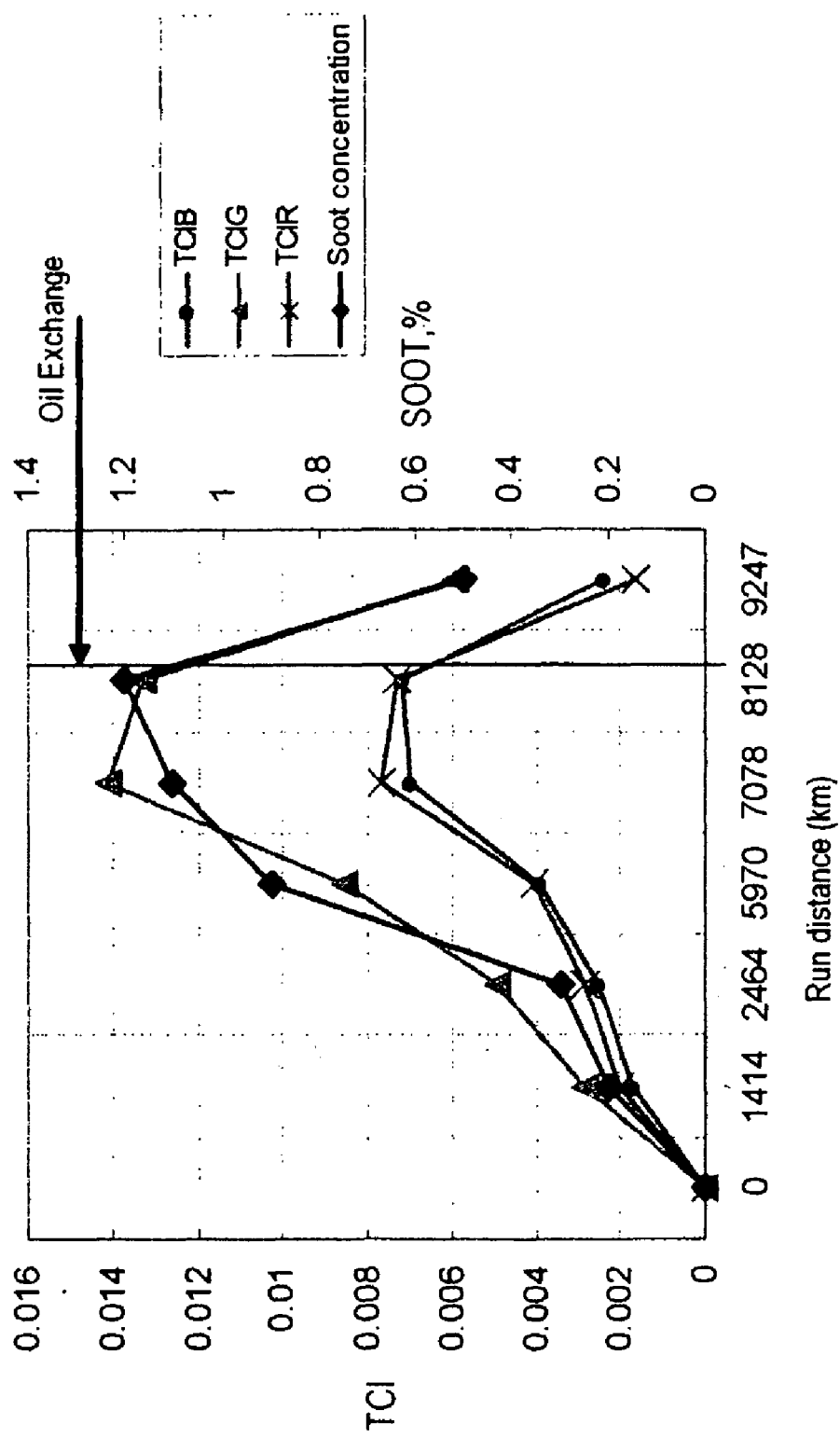
FIG. 8 is a graph illustrating the correlation between a CR parameter and a TAN in a road test of a diesel engine oil.
Figure 9:
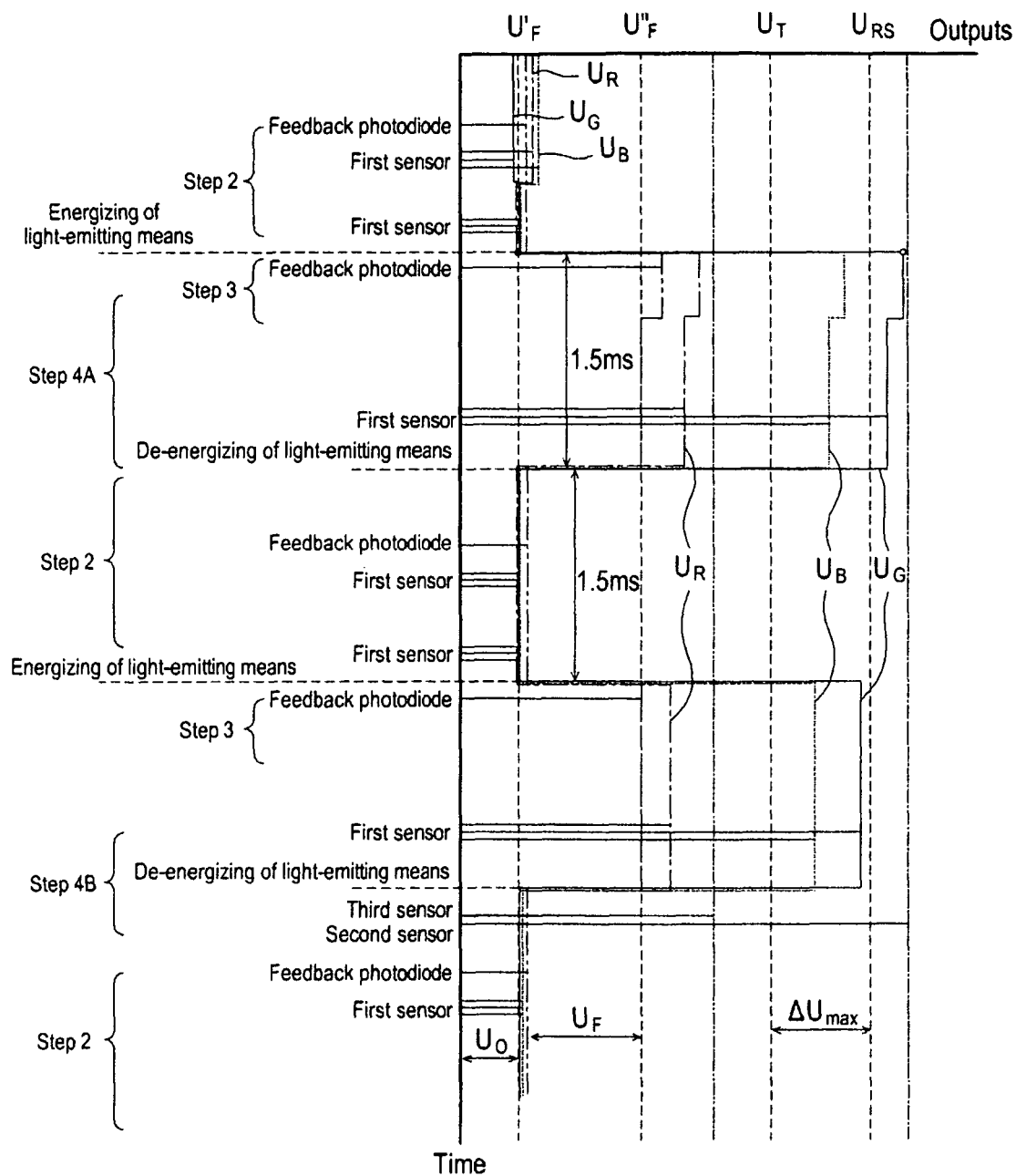
FIG. 9 is a graph illustrating the correlation between a TCI parameter and soot content in a road test of diesel engine oil.

FIGS. 8 and 9 are graphs showing road test results of a diesel engine oil (API CH-4 10W/30), which was taken from a diesel car at different run distances. A full run distance of the car was 9750 km before the test. This corresponds to a run distance of 0 km in the illustrated graphs. Each volume of a sample was 300 ml. When sampled, the same volume (300 ml) of fresh oil was added to a crankcase. The volume of the crankcase of the tested car was 6,000 ml. After 7th sampling (9247 km), the oil was exchanged. The first parameter of CR and the second parameter of TCI were measured by the oil monitoring apparatus employing the probe 300 of the second embodiment in a laboratory. The probe was submerged in the oil sample contained in a glass beaker. A TAN (Total Acid Number), which may be determined by titration method, is a measure of a concentration of acidic decomposition products existing in the oil. The TAN are expected to increase along with the oil degradation. FIG. 8 shows correlation between the first parameter of CR and the TAN. It is evident from the correlation between the CR and the TAN that the CR gives reliable estimation of chemical oil condition. Further, soot content was estimated by an Infacal Soot Meter (Wilks Enterpricse Inc.) as a major contaminant of diesel oil. FIG. 9 shows correlation between the second parameter of TCI and read values from the Soot Meter (soot concentration).

In embodiments of the present disclosure, the calculated chromatic ratio CR and total contamination indexes $TCI_R$, $TCI_G$ and $TCI_B$ may estimate the chemical deterioration and total contamination of oil. The parameters CR, $TCI_R$, $TCI_G$ and $TCI_B$ may be displayed on the monitor 151.

Measured values of the chromatic ratio CR and total contamination indexes $TCI_R$, $TCI_C$ and $TCI_B$ may be compared with their preliminarily stored threshold values.

If the chromatic ratio CR is less than the threshold values, then the oil is evaluated to have a good chemical condition. If the chromatic ratio CR and the change in optical intensity at all wavelength range are above the threshold values, then the oil is in an unacceptable chemical condition.

If the changes in optical intensities at all wavelength ranges are below the threshold value, then the oil has a satisfactory level of total contamination. If the changes in optical intensity at all wavelength ranges are above the threshold value, then the oil has an unacceptable level of total contamination.

If the chromatic ratio and the changes in optical intensity in the blue, green and red wavelength ranges are below their threshold values, then the oil has a good condition. If the chromatic ratio and the changes in optical intensity in the blue, green and red wavelength ranges are above their threshold values, then the oil is determined to be in an unacceptable condition.

Embodiments of the present disclosure may provide an oil monitoring apparatus. The oil monitoring apparatus may monitor simultaneously and successively various parameters, which are related to the deterioration of the oil and to the physical properties of oil for estimating the operation of equipment utilizing the oil, by means of a single detecting device. The oil monitoring apparatus may estimate an optimal time of oil exchange and the operation of the equipment in real time and in a timely manner.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An oil monitoring apparatus, comprising:
 a housing mounted to a member containing oil therein so as to be in contact therewith;
 a first sensor mounted to the housing, the first sensor including:
  an optical passing element with an interface in contact with the oil;
  a light-emitting means for emitting a light to the optical passing element; and
  a color-sensing means for measuring respective optical intensities at respective red, green and blue wavelength ranges of a light passing through the oil via the optical passing element and the interface and for outputting respective signals;
 a second sensor mounted to the housing for measuring water content of the oil and outputting a signal;
 a third sensor mounted to the housing for measuring temperature of the oil and outputting a signal; and
 a control unit including a processor, the processor being configured to calculate a ratio value and a variation value from the respective signals outputted from the color-sensing means, the ratio value being defined by a ratio of an optical intensity at the red wavelength range to an optical intensity at the green wavelength range, the variation value being defined by variations in optical intensity at the respective red, green and blue wavelength ranges between an initial condition and a current condition of the oil, the processor being configured to further calculate a relative saturation of the oil by water from the output signals of the second sensor and a temperature value of the oil from the output signals of the third sensor, the processor being configured to monitor the ratio value, the variation value, the relative saturation and the temperature value.

2. The oil monitoring apparatus of claim 1,
 wherein the optical passing element comprises first and second optical windows spaced apart from and faced to each other;
 wherein the light-emitting means contacts a back face of the tlrst first optical window that is disposed opposite a face of the first optical window, the first optical window being disposed to face the second optical window; and
 wherein the color-sensing means contacts a back face of the second optical window that is disposed opposite a face of the second optical window, the second optical window being disposed to face the first optical window.

3. The oil monitoring apparatus of claim 1,
 wherein the optical passing element comprises a cylindrical body having a refractive index higher than that of the oil, the light being incident on and outgoing from one end of the cylindrical body, the cylindrical body having a light-reflection member at an opposite end thereof; and
 wherein the first sensor further includes a first optical fiber for interconnecting one end of the light-emitting means and the one end of the cylindrical body and a second optical fiber for interconnecting one end of the color-sensing means and the one end of the cylindrical body.

4. The oil monitoring apparatus of claim 3,
 wherein the housing includes a hollow portion having through-holes for flowing in and out of the oil therethrough; and
 wherein the cylindrical body is fixed to one wall of the hollow portion at the one end thereof and to an opposite wall of the hollow portion at the opposite end thereof.

5. The oil monitoring apparatus of claim 1,
 wherein the optical passing element comprises a polyhedral body having a refractive index higher than that of the oil, the polyhedral body having a light-incident face through which a light is incident and a light-outgoing face through which a light outgoes; and
 wherein the light-emitting means is positioned such that an optical axis of an emitted light is normal to the light-incident face and the color-sensing means is positioned such that an optical axis of a received light is normal to the light-outgoing face.

6. The oil monitoring apparatus of claim 3 or 5,
 wherein the processor is configured to normalize a plurality of output signals of the optical intensities at the green and blue wavelength ranges to a depth by which a light at the red wavelength range penetrates from the optical passing element to the oil; and
 wherein the processor is configured to calculate the ratio value, the variation value of the optical intensity at the green wavelength range, and the variation value of the optical intensity at the blue wavelength range.

7. The oil monitoring apparatus of claim 5, wherein the light-incident face and the light-outgoing face are chamfered off so as to satisfy a condition of total internal reflection.

8. The oil monitoring apparatus of claim 1, wherein the apparatus further comprises a sensor monitoring unit, the sensor monitoring unit including:
 an optical radiation measuring means disposed adjacent to the light-emitting means for measuring an optical radiation of the light-emitting means and outputting signals; and
 a current driver for adjusting a current fed to the light-emitting means; and wherein the processor is configured to control the current driver based on the output signals of the optical radiation measuring means.

9. The oil monitoring apparatus of claim 1, wherein the apparatus further comprises a signal calibrating unit, the signal calibrating unit including:
an amplifier for amplifying and transmitting the signals of the color-sensing means to the processor; and
a feedback regulator controlled by the processor for adjusting the signals of the color-sensing means transmitted by the amplifier;
wherein the control unit further includes a gain amplifier for adjusting a gain of the output signals of the amplifier; and
wherein the processor is configured to compare the output signal of the amplifier with a preset minimal critical value and a preset maximal critical value, to increase and decrease the gain of the gain amplifier when the output signal of the amplifier exceeds the minimal critical value and the maximal critical value, and to calculate the ratio value and the variation value when the output signal of the amplifier is between the minimal critical value and the maximal critical value.

10. The oil monitoring apparatus of claim 1, further comprising a display unit controlled by the processor for displaying the ratio value, the variation value, the relative saturation and the temperature value.

11. The oil monitoring apparatus of claim 1, further comprising a communication unit including an interface for communication between the processor and a host computer.

12. An oil monitoring apparatus, comprising:
a probe including:
a housing mounted to a member containing oil therein so as to be in contact therewith;
a first sensor mounted to the housing for measuring optical intensities of a light passing through the oil and outputting signals;
a second sensor mounted to the housing for measuring a water content of the oil and outputting a signal; and
a third sensor mounted to the housing for measuring a temperature of the oil and outputting a signal; and
an analyzing module in-line connected to one of the first sensor, the second sensor, the third sensor, or any combination thereof, for analyzing conditions of the oil;
wherein the first sensor includes:
an optical passing element with an interface in contact with the oil;
a light-emitting means for emitting a light to the optical passing element; and
a color-sensing means for measuring respective optical intensities at respective red, green and blue wavelength ranges of a light passing through the oil via the optical passing element and the interface and outputting respective signals; and
wherein the analyzing module comprises a control unit including a processor configured to calculate the output signals of the first, second and third sensors,
wherein the processor is configured to calculate a first parameter and a second parameter from the output signals of the first sensor, a third parameter from the output signals of the second sensor and a fourth parameter from the output signals of a fourth sensor, the first parameter being defined by a ratio value of an output at the red wavelength range to an output at the green wavelength range, the second parameter being defined by a variation value in optical intensity at the respective red, green and blue wavelength ranges between an initial condition and a current condition of the oil, the third parameter being defined by a relative saturation of the oil by water, the fourth parameter being defined by a temperature of the oil,
wherein the processor is configured to compare the first to fourth parameters with respective threshold values thereof.

13. The oil monitoring apparatus of claim 12,
wherein the optical passing element comprises first and second optical windows spaced apart from and faced to each other;
wherein the light-emitting means contacts a back face of the first optical window that is disposed opposite a face of the first optical window, the first optical window being disposed to face the second optical window; and
wherein the color-sensing means contacts a back face of the second optical window that is disposed opposite a face of the second optical window, the second optical window being disposed to face the first optical window.

14. The oil monitoring apparatus of claim 12, wherein the housing includes a hollow portion having through-holes for flowing in and out of the oil therethrough;
wherein the optical passing element comprises a cylindrical body having a refractive index higher than that of the oil, the light being incident on and outgoing from one end of the cylindrical body, the cylindrical body having a light-reflection member at an opposite end thereof;
wherein the cylindrical body is fixed to one wall of the hollow portion at the one end thereof and to an opposite wall of the hollow portion at the opposite end thereof; and
wherein the first sensor further includes a first optical fiber for interconnecting one end of the light-emitting means and the one end of the cylindrical body and a second optical fiber for interconnecting one end of the color-sensing means and the one end of the cylindrical body.

15. The oil monitoring apparatus of claim 12,
wherein the optical passing element comprises a polyhedral body having a refractive index higher than that of the oil, the polyhedral body having a light-incident face through which a light is incident and a light-outgoing face through which a light outgoes;
wherein the light-incident face and the light-outgoing face are chamfered off so as to satisfy a condition of total internal reflection; and
wherein the light-emitting means is positioned such that an optical axis of an emitted light is normal to the light-incident face and the color-sensing means is positioned such that an optical axis of a received light is normal to the light-outgoing face.

16. The oil monitoring apparatus of claim 14 or 15,
wherein the processor is configured to normalize a plurality of output signals of the optical intensities at the green and blue wavelength ranges to a depth by which a light at the red wavelength range penetrates from the optical passing element to the oil; and
wherein the processor is configured to calculate the first and second parameters.

17. The oil monitoring apparatus of claim 12, wherein the analyzing module further comprises a sensor monitoring unit, the sensor monitoring unit including:

an optical radiation measuring means disposed adjacent to the light-emitting means for measuring an optical radiation of the light-emitting means and outputting signals; and a current driver for adjusting a current fed to the light-emitting means; and wherein the processor is configured to control the current driver based on the output signals of the optical radiation measuring means.

18. The oil monitoring apparatus of claim 12, wherein the analyzing module further comprises a signal calibrating unit, the signal calibrating unit including:

an amplifier for amplifying and transmitting the signals of the color-sensing means to the processor; and a feedback regulator controlled by the processor for adjusting the signals of the color-sensing means transmitted by the amplifier;

wherein the control unit further includes a gain amplifier for adjusting a gain of the output signals of the amplifier; and wherein the processor is configured to compare the output signal of the amplifier with a preset minimal critical value and a preset maximal critical value, to increase and decrease the gain of the gain amplifier when the output signal of the amplifier exceeds the minimal critical value and the maximal critical value, and to calculate the ratio value and the variation value when the output signal of the amplifier is between the minimal critical value and the maximal critical value.

19. The oil monitoring apparatus of claim 12, wherein the analyzing module further comprises a display unit controlled by the processor for displaying the first to fourth parameters.

20. The oil monitoring apparatus of claim 1 or 12, wherein the light-emitting means includes one of a RGB LED and a white LED.

21. The oil monitoring apparatus of claim 1 or 12, wherein the color-sensing means includes a color sensor.

22. The oil monitoring apparatus of claim 1 or 12, wherein the second sensor includes an air humidity sensor with an oleophobic material coated on a surface brought into contact with the oil.

* * * * *